(12) United States Patent
Ryu et al.

(10) Patent No.: US 9,169,263 B1
(45) Date of Patent: Oct. 27, 2015

(54) METHOD FOR PREPARING HIGH-PURITY ANHYDROSUGAR ALCOHOL USING SEQUENTIAL COMBINATION OF THIN FILM DISTILLATION AND SHORT PATH DISTILLATION

(71) Applicant: SAMYANG GENEX CORPORATION, Seoul (KR)

(72) Inventors: Hoon Ryu, Daejeon (KR); Young Jae Jung, Daejeon (KR); Jin Kyung Kim, Daejeon (KR); Do Hyun Kyung, Daejeon (KR); Hyuk Min Park, Incheon (KR); Seong Ho Cho, Seoul (KR)

(73) Assignee: SAMYANG GENEX CORPORATION, Seoul (KR)

( * ) Notice: Subject to any disclaimer, the term of this patent is extended or adjusted under 35 U.S.C. 154(b) by 0 days.

(21) Appl. No.: 14/441,406

(22) PCT Filed: Nov. 6, 2013

(86) PCT No.: PCT/KR2013/009988
§ 371 (c)(1),
(2) Date: May 7, 2015

(87) PCT Pub. No.: WO2014/073843
PCT Pub. Date: May 15, 2014

(30) Foreign Application Priority Data

Nov. 8, 2012 (KR) .......... 10-2012-0126079

(51) Int. Cl.
*C07D 493/04* (2006.01)
*C07D 307/20* (2006.01)
*B01D 3/00* (2006.01)

(52) U.S. Cl.
CPC .............. *C07D 493/04* (2013.01); *B01D 3/009* (2013.01)

(58) Field of Classification Search
CPC .......................... C07D 493/04; C07D 307/20
See application file for complete search history.

(56) References Cited

U.S. PATENT DOCUMENTS

| | | | |
|---|---|---|---|
| 7,439,352 B2 | 10/2008 | Moore et al. | |
| 2004/0152907 A1 | 8/2004 | Moore et al. | |

FOREIGN PATENT DOCUMENTS

| | | |
|---|---|---|
| JP | 2849464 B2 | 1/1999 |
| JP | 4370280 B2 | 11/2009 |
| KR | 10-1079518 B1 | 11/2011 |
| KR | 10-2012-0066904 A | 6/2012 |
| KR | 10-1172615 B1 | 8/2012 |
| WO | WO 2012/081785 A1 | 6/2012 |

OTHER PUBLICATIONS

International Search Report, issued in PCT/KR2013/009988, dated Feb. 26, 2014.

*Primary Examiner* — Sun Jae Yoo
(74) *Attorney, Agent, or Firm* — Birch, Stewart, Kolasch & Birch, LLP

(57) ABSTRACT

The present invention relates to a technique for preparing an anhydrosugar alcohol using hydrogenated sugar as a raw material and, more specifically, to a technique for preparing a high-purity anhydrosugar alcohol (in particular, isosorbide, isomannide, isoidide, and the like) having a purity of 98% or higher and containing less than 0.1% of sorbitol and a sorbitan isomer, which are impurities, in a high total distillation yield of 94% or higher (more preferably, 95% or higher) by adding an acid to hydrogenated sugar (for example, hexitol) to convert same to an anhydrosugar alcohol, and then distilling the converted liquid over two or more stages by sequentially using a combination of an external condenser type wiped film evaporator and an internal condenser type short path evaporator.

13 Claims, 1 Drawing Sheet

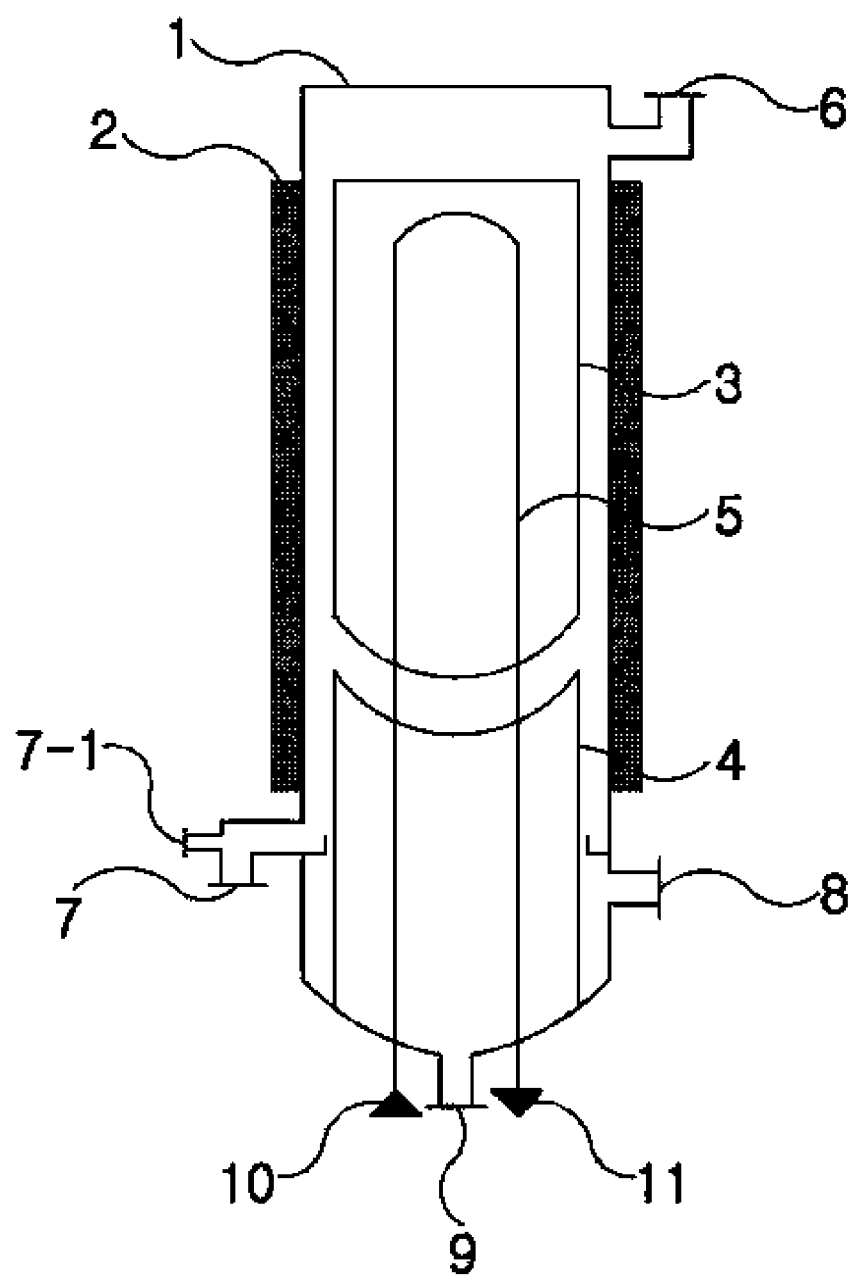

METHOD FOR PREPARING HIGH-PURITY ANHYDROSUGAR ALCOHOL USING SEQUENTIAL COMBINATION OF THIN FILM DISTILLATION AND SHORT PATH DISTILLATION

TECHNICAL FIELD

The present invention relates to a technology for producing anhydrosugar alcohol by using hydrogenated sugar as raw material, and more specifically a technology capable of producing highly pure anhydrosugar alcohol (particularly, isosorbide, isomannide, isoidide, etc.) having a purity of 98% or higher and a content of sorbitol and sorbitan isomer as impurities of less than 0.1% with a distillation yield of 94% or higher (more preferably, 95% or higher) by the conversion of hydrogenated sugar (e.g., hexitol) to anhydrosugar alcohol by addition of an acid thereto, and distillation of the resulting liquid of the conversion reaction in two or more stages by sequential use of a combination of an external condenser type, wiped-film evaporator and an internal condenser type, short-path evaporator.

BACKGROUND ART

Hydrogenated sugar (also referred to as "sugar alcohol") means a compound obtained by adding hydrogen to the reductive end group in sugar, and generally has a chemical formula of $HOCH_2(CHOH)_nCH_2OH$ wherein n is an integer of 2 to 5. According to the carbon number, hydrogenated sugar is classified into tetritol, pentitol, hexitol and heptitol (4, 5, 6 and 7 carbons, respectively). Among them, hexitol having 6 carbons includes sorbitol, mannitol, iditol, galactitol, etc. and in particular, sorbitol and mannitol are very useful materials.

Anhydrosugar alcohol has a diol form with two hydroxyl groups in the molecule, and can be produced by using hexitol derived from starch (for example, Korean Patent No. 10-1079518 and Korean Laid-open Patent Publication No. 10-2012-0066904). Because anhydrosugar alcohol is an environmentally friendly material derived from recyclable natural resources, it has received much interest for a long time and researches on its production continue to proceed. Among such anhydrosugar alcohols, isosorbide produced from sorbitol has the widest industrial applicability at present.

Anhydrosugar alcohol can be used in various fields including treatment of heart and blood vessel diseases, medicaments such as patch adhesive, mouthwash, etc., solvents for compositions in the cosmetics industry, emulsifiers in the food industry, etc. In addition, it can increase the glass transition temperature of polymer materials like polyester, PET, polycarbonate, polyurethane, epoxy resin, etc., and improve the strength of such materials. Furthermore, because anhydrosugar alcohol is an environmentally friendly material derived from natural resources, it is very useful in the plastics industry such as bioplastics and the like. It is also known that anhydrosugar alcohol can be used as an adhesive, environmentally friendly plasticizer, biodegradable polymer, and environmentally friendly solvent for water-soluble lacquer.

As such, anhydrosugar alcohol is receiving much interest because of its wide applicability, and the level of practical industrial application thereof is increasing. However, the conventional methods of producing anhydrosugar alcohol have limitations of high cost for the catalyst used in the dehydration reaction, low conversion rate, and low yields of distillation and purification, etc.

In order to produce anhydrosugar alcohol economically, it is essential to employ a technology of distilling anhydrosugar alcohol from the resulting liquid of conversion reaction within a short time with high yield and high purity.

As a distillation technology of distilling the conversion liquid after dehydration reaction, batch distillation or simple distillation—wherein anhydrosugar alcohol is simply distilled under reduced pressure directly after the conversion reaction in the reactor—is known.

By batch distillation or simple distillation, however, commercial-scale economical production is difficult since the distillation time is long. In addition, if the resulting liquid of a conversion reaction is distilled at a low temperature (e.g., 170° C. or lower), the distillation time increases, and if distilled at a relatively high temperature (e.g., 170° C. or higher), the distillation time decreases but the anhydrosugar alcohol is thermally decomposed at 170° C. or higher, and byproducts such as formic acid, furfural, etc. are generated, by which the purity of the product and the pH of the distillate are lowered. That is, as compared with the wiped-film evaporation explained below, since batch distillation or simple distillation requires relatively longer retention time of distillate and higher distillation temperature, thermal decomposition of alcohol is induced, generating the problem of lowering purity and yield of the distillate. To prevent such a thermal decomposition, use of an additive is required.

In order to overcome the deficiencies of batch distillation or simple distillation in distilling anhydrosugar alcohol from the resulting liquid of a conversion reaction, U.S. Pat. No. 7,439,352 suggested a technology of distilling anhydrosugar alcohol by wiped-film evaporation using an external condenser. In the wiped-film evaporation technology disclosed in this US patent, the condenser is operated outside of the distillator. In this type, however, the maximum vacuum circumstance that can be formed in the distillator technically is 1 mmHg; under such a vacuum degree the distillation temperature should be 170° C. or higher in order to conduct the distillation effectively. However, as stated earlier the anhydrosugar alcohol such as isosorbide is thermally decomposed at a distillation temperature of 170° C. or higher, and thereby the distillation yield and distillation purity are lowered. Accordingly, in the above US patent, the purity of the single-step distillation product is 97.1% or the like and the distillation yield is 80% or the like. However, such levels of purity and yield are still not suitable for a commercial-scale mass-production process.

In the above US patent, the isosorbide purity is increased to 99.9% through distillation of two (2) stages. However, the overall distillation yield is low (first stage/second stage yield 77.5%). To resolve the problem of such a low overall distillation yield, the above US patent employs a separate process for crystallizing the residue of the two-stage distillation and recovering isosorbide therefrom. However, in the overall process flow as such, the isosorbide is produced by two separate processes consequentially, which makes the uniform quality control much more difficult than a single-process production.

Therefore, a technology of producing anhydrosugar alcohol, which can provide high purity (e.g., 98% or higher) and a content of sorbitol and sorbitan isomer as impurities of less than 0.1% with a high overall distillation yield (e.g., 94% or higher, more preferably, 95% or higher), is required.

CONTENTS OF THE INVENTION

Problems to be Solved

To resolve the problems of the prior arts as explained above, the present invention has an object of providing a method which can produce anhydrosugar alcohol with a purity of 98% or higher and a content of sorbitol and sorbitan isomer as impurities of less than 0.1% with a distillation yield of 94% or higher—i.e., with a high purity and a high yield at the same time.

Technical Means

To achieve the above-stated object, the present invention provides a method for producing anhydrosugar alcohol comprising the steps of: converting hydrogenated sugar to anhydrosugar alcohol by dehydration reaction, and distilling the resulting liquid of the converting step in two or more stages by sequential use of a combination of an external condenser type, wiped-film evaporator and an internal condenser type, short-path evaporator.

According to a preferred aspect of the present invention, the internal condenser type, short-path evaporator comprises an internal condenser, an input line for raw material, an output line for distillation residue, a vacuum line and an output line for distillate.

According to a more preferred aspect of the present invention, when the distilling step is conducted with using the internal condenser type, short-path evaporator, the inside of the evaporator is depressurized by pressure reduction through the vacuum line and additionally through the output line for distillation residue.

Effect of the Invention

According to the present invention, it is possible to easily produce anhydrosugar alcohol with a high purity (98% or higher) and a content of sorbitol and sorbitan isomer as impurities of less than 0.1% with a high distillation yield (overall distillation yield of 94% or higher, more preferably, 95% or higher).

BRIEF EXPLANATION OF THE DRAWINGS

FIG. 1 schematically represents a structure of a preferable embodiment of an internal condenser type, short-path evaporator which can be used in the method for producing anhydrosugar alcohol of the present invention.

CONCRETE EXPLANATION TO CARRY OUT THE INVENTION

The present invention is explained in more detail below.

The method for producing anhydrosugar alcohol of the present invention comprises a step of converting hydrogenated sugar to anhydrosugar alcohol by dehydration reaction.

Hydrogenated sugar, also generally referred to as sugar alcohol, means a compound obtained by adding hydrogen to the reductive end group in sugar. According to the carbon number, hydrogenated sugar is classified into tetritol, pentitol, hexitol and heptitol (4, 5, 6 and 7 carbons, respectively). Among them, hexitol, having 6 carbons, includes sorbitol, mannitol, iditol, galactitol, etc.—in particular, sorbitol and mannitol are very useful materials.

As used herein, the expression "anhydrosugar alcohol" means any material that is obtained by removing one or more water molecules from the original inner structure of said hydrogenated sugar (or sugar alcohol) in one or more steps by any method.

In the present invention, hexitol is preferably used as the hydrogenated sugar, and more preferably, the hydrogenated sugar for use is selected from sorbitol, mannitol, iditol and mixtures thereof.

Accordingly, in the present invention, dianhydrohexitol—which is the dehydrated product of hexitol—is preferably obtained as the anhydrosugar alcohol, and more preferably, the obtained anhydrosugar alcohol is selected from isosorbide (1,4-3,6-dianhydrosorbitol), isomannide (1,4-3,6-dianhydromannitol), isoidide (1,4-3,6-dianhydro iditol) and mixtures thereof. Among them, isosorbide is particularly useful for industrial and medicinal application.

The hydrogenated sugar is converted to anhydrosugar alcohol by dehydration reaction. There is no special limitation in the method of dehydrating hydrogenated sugar, and any conventionally known method in this field may be utilized as it is or with proper modification.

It is preferable to use an acid catalyst in dehydrating hydrogenated sugar to convert it to anhydrosugar alcohol, and more preferably, acid mixture of a first acid and a second acid can be used. As for the acid catalyst, in the case of a single acid catalyst, sulfuric acid, hydrochloric acid, phosphoric acid, etc. can be used; and in the case of an acid mixture, sulfuric acid can be used as the first acid, and one or more sulfur-containing acids or salts thereof selected from the group consisting of p-toluenesulfonic acid, methanesulfonic acid, ethanesulfonic acid, benzenesulfonic acid, naphthalenesulfonic acid and aluminum sulfate can be used as the second acid. The acid catalyst is preferably used in an amount of from 0.5 to 10 parts by weight per 100 parts by weight of the hydrogenated sugar (e.g., hexitol). If the amount of acid catalyst is much less than the above range, the conversion time to anhydrosugar alcohol may become excessively long. On the other hand, if the amount of acid catalyst is much greater than the above range, sugar polymer may be increasingly generated and the conversion rate may be lowered.

According to an embodiment of the present invention, the step of converting hydrogenated sugar to anhydrosugar alcohol may be conducted in the presence of an acid catalyst as explained above, at a temperature of from 105 to 200° C. (more preferably, 110 to 150° C.) under a pressure of from 1 to 100 mmHg (more preferably, 1 to 50 mmHg) for 1 to 10 hours (more preferably, 2 to 5 hours), but it is not limited thereto.

In the case of using an acid catalyst during the dehydration reaction of hydrogenated sugar, it is preferable to neutralize the reaction product liquid. The neutralization may be conducted by, after the dehydration reaction, cooling the reaction product liquid (e.g., to 100° C. or lower) and adding thereto conventional alkali such as sodium hydroxide. The neutralized reaction product liquid preferably has a pH of 6 to 8.

According to a preferable embodiment of the method for producing anhydrosugar alcohol of the present invention, the resulting liquid of the step of converting hydrogenated sugar to anhydrosugar alcohol may be pre-treated before being fed to the first distilling step. The purpose of the pre-treatment is to remove moisture and a low-boiling-point substance(s) remaining in the resulting liquid of the converting step, and may be conducted conventionally at a temperature of from 90° C. to 110° C. under a pressure of 10 mmHg to 100 mmHg for 1 hour or longer (e.g., 1 to 4 hours), but it is not limited thereto.

The resulting liquid of the step of converting hydrogenated sugar to anhydrosugar alcohol (preferably, the pre-treated resulting liquid as explained above) is distilled in two or more stages by sequential use of a combination of an external condenser type, wiped-film evaporator and an internal condenser type, short-path evaporator.

In the present invention, "wiped-film distillation" means a distillation conducted by using a conventional external condenser type, wiped-film evaporator as disclosed in U.S. Pat.

No. 7,439,352, and it is distinguished from "short-path distillation" conducted thereafter. The short-path distillation is characterized in using an internal condenser type, short-path evaporator as shown in FIG. 1. The short-path distillation is also different from "simple distillation" wherein distillation is conducted without formation of thin film.

In light of the workability and efficiency of the overall process, the distillation of two or more stages is properly the distillation of two or three stages. The two-stage distillation may be conducted in the order of wiped-film distillation; and short-path distillation, and the three-stage distillation may be conducted in the order of wiped-film distillation; short-path distillation; and short-path distillation, but it is not limited thereto. As long as short-path distillation is conducted after wiped-film distillation, any combinations thereof may be used. According to a preferable embodiment of the present invention, when an internal condenser type, short-path evaporator as shown in FIG. 1 is used in a distillation step after wiped-film distillation, high purity and high yield can be achieved simultaneously only by the two-stage distillation of wiped-film distillation; and short-path distillation.

It is preferred that the distillation of two or more stages be conducted in a continuous manner, where the continuous manner includes—as well as distillation using two or more connected evaporators without time discrepancy—distillation using one evaporator wherein after the first distillation is conducted, with no other separate treatment the next one is conducted even though there is a time discrepancy between the first distillation and the next one.

A structure of a preferable embodiment of an internal condenser type, short-path evaporator which can be used in the method for producing anhydrosugar alcohol of the present invention is schematically represented in FIG. 1. The internal condenser type, short-path evaporator 1 according to FIG. 1 comprises internal condenser 5, input line for raw material 6, output line for distillation residue 7, branch line for vacuum formation 7-1, vacuum line 8 and output line for distillate 9, and further comprises heating jacket 2 for heating, wiper 3, condenser guard 4 and cooler input/output lines 10 and 11, respectively. The internal condenser type, short-path evaporator which can be used in the present invention is not limited to that of the structure shown in FIG. 1 (for example, the branch line for vacuum formation 7-1 may be omitted), and if necessary, it may further comprise additional components other than the above-explained ones, and the forms thereof may be various.

There is no special limitation in the external condenser type, wiped-film evaporator which can be used in the method for producing anhydrosugar alcohol of the present invention. For example, among conventional external condenser type, wiped-film evaporators including that disclosed in U.S. Pat. No. 7,439,352, proper one can be selected and used.

The distillation using an external condenser type, wiped-film evaporator can be conducted effectively under a temperature condition of preferably from 120 to 250° C., more preferably from 120 to 220° C., and still more preferably from 150 to 200° C. In case of using an external condenser type, wiped-film evaporator, if the distillation temperature is lower than 120° C., the distillation of anhydrosugar alcohol may not be conducted effectively. If the distillation temperature is higher than 250° C., anhydrosugar alcohol may be carbonized or polymer material may be generated, and the color will become dark due to the formation of coloring substance, rendering decolorization difficult. Furthermore, anhydrosugar alcohol is thermally decomposed at high temperature and thus byproducts such as formic acid, furfural, etc. are generated, and they lower the purity and pH of the resulting liquid of distillation, which is not industrially preferable.

In case of using an external condenser type, wiped-film evaporator, under the above preferable temperature condition, the pressure condition (inside the reactor) of the distillation is preferably 10 mmHg or less (e.g., 0.0001 to 10 mmHg, more concretely, 0.0001 to 8 mmHg), more preferably 5 mmHg or less (e.g., 0.001 to 5 mmHg), and still more preferably 3 mmHg or less (e.g., 0.01 to 3 mmHg, more concretely 0.01 to 2 mmHg). If the distillation pressure is greater than 10 mmHg, the distillation temperature should be elevated in order to distill anhydrosugar alcohol and in such a case, the aforesaid problems may be generated. On the other hand, excessively low distillation pressure is not preferable since an extra cost would be necessitated for a high-vacuum device to lower the distillation pressure.

The distillation using an internal condenser type, short-path evaporator can be conducted effectively under a temperature condition of preferably from 100 to 250° C., more preferably from 100 to 200° C., and still more preferably from 110 to 170° C. In case of using an internal condenser type, short-path evaporator, if the distillation temperature is lower than 100° C., the distillation of anhydrosugar alcohol may not be conducted effectively. If the distillation temperature is higher than 250° C., anhydrosugar alcohol may be carbonized or polymer material may be generated, and the color will become dark due to the formation of coloring substance, rendering decolorization difficult. Furthermore, anhydrosugar alcohol is thermally decomposed at high temperature and thus byproducts such as formic acid, furfural, etc. are generated, and they lower the purity and pH of the resulting liquid of distillation, which is not industrially preferable.

In case of using an internal condenser type, short-path evaporator, under the above preferable temperature condition, the pressure condition (inside the reactor) of the distillation is preferably 10 mmHg or less (e.g., 0.0001 to 10 mmHg, more concretely, 0.0001 to 8 mmHg), more preferably 5 mmHg or less (e.g., 0.001 to 5 mmHg), and still more preferably 1 mmHg or less (e.g., 0.01 to 1 mmHg, more concretely 0.01 to 0.8 mmHg). If the distillation pressure is greater than 10 mmHg, the distillation temperature should be elevated in order to distill anhydrosugar alcohol and in such a case, the aforesaid problems may be generated. On the other hand, excessively low distillation pressure is not preferable since an extra cost would be necessitated for a high-vacuum device to lower the distillation pressure.

According to a preferable embodiment of the present invention, when the distillation using an internal condenser type, short-path evaporator is conducted, in addition to the depressurization of the inside of the evaporator through the vacuum line it is possible to further depressurize it through the output line for distillation residue.

In the present invention, improvement of yield and purity in the distilling step can be achieved simultaneously by placing an external condenser type, wiped-film evaporator in the first stage to increase the distillation yield and thereafter conducting further distillation by an internal condenser type, short-path evaporator to increase the purity of the target product.

In a preferable embodiment of the present invention, in case of using an internal condenser type, short-path evaporator, there is no special limitation in the method of additionally depressurizing the inside of the evaporator through the output line for distillation residue. For example, a vacuum pump connected to the vacuum line can also be connected to the branch line for vacuum formation of the output line for distillation residue, by which the same degree of vacuum can be applied to the output line for distillation residue and the vacuum line. Alternatively, a separate vacuum pump can be connected to the branch line for vacuum formation of the output line for distillation residue, by which an independent degree of vacuum from the vacuum line can be applied to the output line for distillation residue.

With reference to FIG. 1, an embodiment of conducting distillation by connecting the same vacuum pump to the vacuum line and the branch line for vacuum formation of the output line for distillation residue in the internal condenser type, short-path evaporator is explained below.

In conventional short-path distillation, a vacuum pump (not shown) is connected to the vacuum line 8 only, and accordingly the relative pressure relationship inside the evaporator is: [vacuum line 8<inside of condenser guard 4<outside of condenser guard 4=output line for distillation residue 7]. In this, because the pressure at the output line for distillation residue 7 is greater than those of the inside and outside of condenser guard 4, the flow of distillation residue is disturbed. To the contrary, if the same vacuum pump is connected to the vacuum line and the branch line for vacuum formation of the output line for distillation residue 7-1 in the internal condenser type, short-path evaporator and operated according to the preferable embodiment of the present invention, the relative pressure relationship inside the evaporator becomes: [vacuum line 8=output line for distillation residue 7<outside of condenser guard 4=inside of condenser guard 4]. Thus, the high-vacuum state can be maintained more effectively and the flow of distillation residue can also be improved effectively. In the above, "=" means the same or a similar level of pressure.

The method for producing anhydrosugar alcohol of the present invention may further comprise, after the distilling step of two or more stages, a step of conducting post-treatment for the anhydrosugar alcohol resulting from the distillation, wherein the post-treatment is selected from crystallization, adsorbent treatment, ion purification, and a combination thereof.

The crystallization may be conducted by a method of crystallization using a solvent (e.g., acetone) or a method of melt crystallization using no solvent.

The adsorbent treatment is for decolorization and may be conducted by using a conventional adsorbent such as active carbon according to the conventional method of adsorbent treatment. As the active carbon, one or more selected from active carbon groups obtained by activating plant sources such as wooden material, palm, etc. or mineral sources such as brown coal, bituminous coal, soft coal, anthracite coal, etc. may be used.

The purpose of ion purification is to remove ions that may exist in the anhydrosugar alcohol, and it can be conducted 1 time or more using one or more ion exchange resins selected from strong cationic, weak cationic, strong anionic and weak anionic ion exchange resin groups according to the ion types that may exist.

According to a preferable embodiment of the present invention, after converting hexitol as the hydrogenated sugar to anhydrosugar alcohol, the two-stage distillation of the resulting liquid of the converting step in the order of wiped-film distillation; and short-path distillation can provide highly pure anhydrosugar alcohol having purity of 98% or higher, a content of sorbitol and sorbitan isomer as impurities of less than 0.1% (more preferably, less than 0.05%) and improved color of pale yellow, with a distillation yield of 94% or higher (more preferably, 95% or higher), and subsequently conducting crystallization, decolorization by adsorbent and ion purification procedures, etc. can provide white isosorbide.

The present invention is explained in more detail through the following Examples and Comparative Examples. However, the Examples are intended to facilitate understanding of the present invention only, and the scope of the present invention is not limited thereby.

EXAMPLES

Example 1

10,000 g of sorbitol powder (D-sorbitol, Samyang Genex Inc.) was fed into a batch reactor equipped with an agitator and melted by heating to 110° C. 100 g of sulfuric acid (Duksan Chemical) and 42 g of methanesulfonic acid (Duksan Chemical) were added thereto, and the reactor was heated to about 140° C. Dehydration reaction was conducted under a reduced pressure condition of about 30 mmHg to convert sorbitol to anhydrosugar alcohol. After the dehydration reaction was completed, the reaction mixture was cooled to 110° C., and about 300 g of 50% sodium hydroxide solution (Samjeon Pure Chemical) was added thereto to neutralize the resulting reaction liquid. The resulting neutralized liquid was set to be at 100° C. and then concentrated under a reduced pressure condition of 40 mmHg or less for 1 hour or longer to remove the moisture and low-boiling-point substance present in the resulting liquid. After the neutralization and moisture removal were completed, the resulting liquid was analyzed. The results were 74% of conversion rate of sorbitol, 1% by weight of sorbitan and sorbitan isomer content in the resulting liquid, and 15% of other polymer content.

The resulting liquid after the neutralization and moisture removal was fed into an external condenser type, wiped-film evaporator, and subject to the first stage distillation under conditions of 185° C. of distillation temperature and 1.3 mmHg of evaporator inside pressure. The resulting distillate of the first stage distillation was then fed into an internal condenser type, short-path evaporator having the structure shown in FIG. 1, and subject to the second stage distillation under conditions of 146° C. of distillation temperature and 1.3 mmHg of evaporator inside pressure. At that time, the distillation was conducted by connecting a vacuum pump to the vacuum line, and additionally to the branch line for vacuum formation of the output line for distillation residue.

The isosorbide obtained through the two-stage distillation showed the purity of 98.2% and the color of pale yellow with the distillation yield of 95% or higher (about 95.2%). The total content of sorbitol and sorbitan isomer was less than 0.05% (about 0.048%).

Gas chromatography (GC, HP) was used to analyze the resulting product.

Conversion rate=[moles of produced anhydrosugar alcohol/moles of fed hexitol(sorbitol)]*100

Distillation yield=[wt % of anhydrosugar alcohol in distillate/wt % of anhydrosugar alcohol in resulting liquid of conversion]*100

Example 2

The resulting liquid of conversion obtained after the neutralization and moisture removal in Example 1 was fed into the external condenser type, wiped-film evaporator, and subject to the first stage distillation under conditions of 185° C. of distillation temperature and 1.3 mmHg of evaporator inside pressure. The resulting distillate of the first stage distillation was then fed into the internal condenser type, short-path evaporator having the structure shown in FIG. 1, and subject to the second stage distillation under conditions of 100° C. of distillation temperature and 0.01 mmHg of evaporator inside pressure. At that time, the distillation was conducted by connecting a vacuum pump to the vacuum line, and additionally to the branch line for vacuum formation of the output line for distillation residue.

The isosorbide obtained through the two-stage distillation showed the purity of 98.2% and the color of pale yellow with the distillation yield of 95% or higher (about 95.2%). The total content of sorbitol and sorbitan isomer was less than 0.05% (about 0.048%).

Example 3

The resulting liquid of conversion obtained after the neutralization and moisture removal in Example 1 was fed into the external condenser type, wiped-film evaporator, and subject to the first stage distillation under conditions of 185° C. of distillation temperature and 1.3 mmHg of evaporator inside pressure. The resulting distillate of the first stage distillation was then fed into the internal condenser type, short-path evaporator having the structure shown in FIG. 1, and subject to the second stage distillation under conditions of 170° C. of distillation temperature and 5.0 mmHg of evaporator inside pressure. At that time, the distillation was conducted by connecting a vacuum pump to the vacuum line, and additionally to the branch line for vacuum formation of the output line for distillation residue.

The isosorbide obtained through the two-stage distillation showed the purity of 98.2% and the color of pale yellow with the distillation yield of 95% or higher (about 95.2%). The total content of sorbitol and sorbitan isomer was less than 0.05% (about 0.048%).

Comparative Example 1

The resulting liquid of conversion obtained after the neutralization and moisture removal in Example 1 was fed into the external condenser type, wiped-film evaporator, and subject to the first stage distillation under conditions of 185° C. of distillation temperature and 2.0 mmHg of evaporator inside pressure. The resulting distillate of the first stage distillation was then refed into the same external condenser type, wiped-film evaporator, and subject to the second stage distillation under conditions of 180° C. of distillation temperature and 2.0 mmHg of evaporator inside pressure.

The isosorbide obtained through the two-stage distillation showed the purity of 96.1% with the distillation yield of 94%.

When the second stage distillation was conducted in an external condenser type, wiped-film evaporator, the effect of improving the purity was worse than that of using an internal condenser type, short-path evaporator.

EXPLANATION OF THE SYMBOLS

1: Short-path evaporator
2: Heating jacket
3: Wiper
4: Condenser guard
5: Internal condenser
6: Input line for raw material
7: Output line for distillation residue
7-1: Branch line for vacuum formation
8: Vacuum line
9: Output line for distillate
10: Cooler input line
11: Cooler output line

The invention claimed is:

1. A method for producing anhydrosugar alcohol comprising the steps of:
   converting hydrogenated sugar to anhydrosugar alcohol by dehydration reaction, and
   distilling the resulting liquid of the converting step in two or more stages by sequential use of a combination of an external condenser type, wiped-film evaporator and an internal condenser type, short-path evaporator.

2. The method for producing anhydrosugar alcohol according to claim 1, wherein the internal condenser type, short-path evaporator comprises an internal condenser, an input line for raw material, an output line for distillation residue, a vacuum line and an output line for distillate.

3. The method for producing anhydrosugar alcohol according to claim 2, wherein when the distilling step is conducted with using the internal condenser type, short-path evaporator, the inside of the evaporator is depressurized by pressure reduction through the vacuum line and additionally through the output line for distillation residue.

4. The method for producing anhydrosugar alcohol according to claim 2, wherein when the distilling step is conducted with using the internal condenser type, short-path evaporator, the degree of vacuum of the vacuum line is the same as the degree of vacuum of the output line for distillation residue.

5. The method for producing anhydrosugar alcohol according to claim 1, wherein the hydrogenated sugar is hexitol and the anhydrosugar alcohol is dianhydrohexitol.

6. The method for producing anhydrosugar alcohol according to claim 1, wherein an acid catalyst is used in the step of converting hydrogenated sugar to anhydrosugar alcohol by dehydration reaction.

7. The method for producing anhydrosugar alcohol according to claim 1, wherein the resulting liquid of the step of converting hydrogenated sugar to anhydrosugar alcohol is pre-treated to remove moisture and low-boiling-point substance before being fed to the first distilling step.

8. The method for producing anhydrosugar alcohol according to claim 1, wherein the distillation using the external condenser type, wiped-film evaporator is conducted under a temperature condition of from 120 to 250° C.

9. The method for producing anhydrosugar alcohol according to claim 1, wherein the distillation using the external condenser type, wiped-film evaporator is conducted under a pressure condition of 10 mmHg or less.

10. The method for producing anhydrosugar alcohol according to claim 1, wherein the distillation using the internal condenser type, short-path evaporator is conducted under a temperature condition of from 100 to 250° C.

11. The method for producing anhydrosugar alcohol according to claim 1, wherein the distillation using the internal condenser type, short-path evaporator is conducted under a pressure condition of 10 mmHg or less.

12. The method for producing anhydrosugar alcohol according to claim 1, wherein the distillate after the distilling step of two or more stages has an anhydrosugar alcohol purity of 98% or higher, a content of sorbitol and sorbitan isomer as impurities of less than 0.1%, and a distillation yield of 94% or higher.

13. The method for producing anhydrosugar alcohol according to claim 1, wherein after the distilling step of two or more stages, a step of post-treatment is further conducted for the anhydrosugar alcohol resulting from the distillation, and wherein the post-treatment is selected from crystallization, adsorbent treatment, ion purification, and a combination thereof.

* * * * *